US009289162B2

(12) United States Patent
Kuhr et al.

(10) Patent No.: US 9,289,162 B2
(45) Date of Patent: Mar. 22, 2016

(54) CONTROL DEVICE FOR A MEDICAL TEST SYSTEM

(75) Inventors: Hans-Juergen Kuhr, Mannheim (DE); Herbert Harttig, Neustadt (DE); Hans-Peter Haar, Wieslech (DE); Hans List, Hesseneck-Kailbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 13/365,404

(22) Filed: Feb. 3, 2012

(65) Prior Publication Data
US 2012/0165698 A1 Jun. 28, 2012

Related U.S. Application Data

(63) Continuation of application No. PCT/EP2010/061301, filed on Aug. 3, 2010.

(30) Foreign Application Priority Data

Aug. 4, 2009 (EP) .................................. 09 167 178

(51) Int. Cl.
*A61B 5/00* (2006.01)
*A61B 5/15* (2006.01)
*A61B 5/145* (2006.01)
*A61B 5/1459* (2006.01)
(Continued)

(52) U.S. Cl.
CPC .............. *A61B 5/1411* (2013.01); *A61B 5/1459* (2013.01); *A61B 5/14532* (2013.01); *A61B 5/157* (2013.01); *A61B 5/15186* (2013.01)

(58) Field of Classification Search
CPC ............. A61B 5/1411; A61B 5/14532; A61B 5/15146
USPC .................................................. 600/573, 583
See application file for complete search history.

(56) References Cited

U.S. PATENT DOCUMENTS

2004/0132167 A1* 7/2004 Rule et al. ................... 435/287.1
2006/0100542 A9* 5/2006 Wong et al. ..................... 600/583
2006/0119304 A1* 6/2006 Farritor et al. ............ 318/568.12
(Continued)

FOREIGN PATENT DOCUMENTS

EP 1669028 A1 * 6/2006
EP 1982653 A1 * 10/2008
WO WO 2005/104949 11/2005

OTHER PUBLICATIONS

International Preliminary Report on Patentability; PCT/EP2010/061301; Oct. 14, 2011.
(Continued)

*Primary Examiner* — Sean Dougherty
*Assistant Examiner* — Daniel Cerioni
(74) *Attorney, Agent, or Firm* — Bose McKinney & Evans LLP

(57) ABSTRACT

The invention concerns a control device for a medical test system which has a lancing element that can be inserted into body tissue to collect body fluid and a lancing drive for the lancing element. A sensor element for body fluid is arranged on the lancing element and a control unit is coupled to the sensor element for detecting a fault when collecting body fluid. In order to improve the success rate, the control unit actuates the lancing drive for an automatic puncture repetition in less than 1 second when a fault, e.g., inadequate wetting of a detection field, occurs.

27 Claims, 3 Drawing Sheets

(51) Int. Cl.
*A61B 5/151* (2006.01)
*A61B 5/157* (2006.01)

(56) References Cited

U.S. PATENT DOCUMENTS

2006/0155317 A1* 7/2006 List ............................. 606/181
2008/0021490 A1 1/2008 Briggs et al.
2009/0192409 A1 7/2009 Wong et al.
2009/0209883 A1* 8/2009 Higgins et al. ................ 600/575
2010/0021947 A1* 1/2010 Emery et al. ................... 435/14

OTHER PUBLICATIONS

International Search Report of the International Searching Authority; PCT/EP2010/061301; Sep. 20, 2010.

* cited by examiner

CONTROL DEVICE FOR A MEDICAL TEST SYSTEM

RELATED APPLICATIONS

This application is a continuation of PCT/EP2010/061301, filed Aug. 3, 2010; which claims priority to EP 09 167 178.4, filed Aug. 4, 2009, both of which are incorporated herein by reference in their entirety.

BACKGROUND

The invention concerns a control device for a medical test system which has a lancing element that can be inserted into body tissue to collect body fluid, a lancing drive for the lancing element, a sensor element for body fluid arranged on the lancing element, and a control unit coupled to the sensor element. In particular, the invention concerns detecting a fault when collecting body fluid.

The repetition of a lancing process to improve blood collection is known for lancing aids with disposable lancets. If the first puncture does not result in an adequate drop of blood, the user tensions the lancing aid again and makes a second puncture with the same lancet which, if necessary, is deeper. The disadvantage of these mechanical lancing devices is the control by the user who must ultimately decide whether to repeat a puncture. The time that has elapsed between two punctures is correspondingly large, typically 10 to 20 seconds, and can hardly be shortened.

A more rapid repetition of punctures is conceivable using electrically operated lancing aids in which the tensioning and/or the actual puncture are initiated by electromechanical components. In EP-A 1 982 653 it is proposed that a check of the success of blood collection is interposed after the first puncture with a lancing element. This should enable the user to manually collect a sample. This type of feedback is achieved by a test element integrated into the blood collection system which is designed to generate a measured value with the blood collected from the first puncture. Such blood sugar measuring systems are therefore also referred to as integrated spot monitoring (ISM) systems. However, such ISM systems must be able to take into account the different skin types as well as human operator errors during blood collection without overburdening or impairing the user. Frequent determination of blood sugar is essential for diabetics as part of a self-monitoring program. A high success rate is desirable for such self-monitoring programs without an unnecessary consumption of test devices.

SUMMARY

The present invention further improves the known devices and helps ensure a successful test procedure with a high degree of convenience for the user.

Exemplary embodiments are based on the idea of enabling a lancing element with an integrated collecting structure to be re-used for a second puncture during the lancing process by means of a type of online detection of the lancing success. Accordingly, it is proposed that in the case of a fault the control unit actuates the lancing drive for an automatic puncture repetition in less than 1 second. This time window is based on the surprising finding that a successful test outcome can be impaired by evaporation processes. Thus, an underdosing can be avoided due to the short automatic process without impeding the collecting process. Such a puncture repetition can then be carried out with a single disposable lancing element with an integrated sensor element so that expensive test devices are not unintentionally wasted. Moreover, additional manipulation of the body tissue during the repetition interval is neither intended nor necessary, thus resulting in a high degree of handling comfort. The first puncture takes place in a reciprocating or forwards and backwards lancing movement where the lancing element is, if necessary, pulled completely out of the body tissue to the starting point before the second puncture in order to enable a uniform lancing process.

In order to take into consideration the identified constraints for skin puncture, it is advantageous that the repetition interval is less than 700 ms, preferably less than 500 ms.

In order for the online detection to be as rapid as possible, it is advantageous that the sensor element is fluidly connected to a section of a collecting channel for body fluid formed on the lancing element, the section preferably not engaging into the body tissue.

When wetted with body fluid the sensor element advantageously generates a signal which can be evaluated as a control signal for the collection of body fluid and also as a measurement signal for a component of the body fluid. A further improvement with regard to the reaction time is derived from the fact that the sensor element generates a control signal that changes discontinuously, in particular, in the form of a step-change in reflectance when it is wetted with body fluid.

In order to achieve short control paths it is advantageous when the sensor element is connected to the control unit by means of at least one signal conductor preferably at least one light guide during the lancing movement of the lancing element.

The sensor element advantageously has two or more detection areas arranged spaced apart from one another to detect a two-dimensional load of body fluid so that underdosing at the site of measurement can be specifically detected.

In this connection it is advantageous when the control unit already detects an absence of wetting or an inadequate wetting of the sensor element with body fluid as a fault during the lancing process in which case, if necessary, different remedial measures can be taken.

Another improvement of user friendliness can be achieved by means of the fact that the control unit can be deactivated by a user of the test system by means of a hardware or software switch.

In this connection it is also advantageous when the control unit has a control loop which automatically adapts lancing parameters for the second puncture such as lancing depth and dwell time of the lancing element in the body tissue.

Another aspect of this disclosure is a test system in particular for blood sugar tests comprising a lancing element that can be inserted into body tissue to collect body fluid and a lancing drive for the lancing element in which a control unit according to the invention is implemented.

It is advantageous for a fastest possible puncture repetition when the lancing drive has an energy store dimensioned for a multiple puncture or several energy stores each dimensioned for a single puncture.

It is also conceivable that the lancing drive has a brushless direct current motor that can be temporary subjected to an overcurrent without damage for a direct transfer of the lancing movement.

A further improvement of the degree of integration results from the fact that the sensor element has a detection field for a component of the body fluid, and that the component as well as the wetting state of the detection field with body fluid can be detected by means of a unitary measuring unit.

In order to optimize sample collection, the lancing element should have a collecting volume of less than 100 nl to collect body fluid, in particular blood.

It is also advantageous when the lancing element has a capillary transport channel to transfer the body fluid onto the sensor element in a transfer time of less than 0.3 s after the skin puncture.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The exemplary embodiments described below are not intended to be exhaustive or to limit the invention to the precise forms disclosed in the following detailed description. Rather, the embodiments are chosen and described so that others skilled in the art may appreciate and understand the principles and practices of the present invention.

The test systems 10 shown in the diagram enable automated sample collection and measured value recording for blood sugar determinations as hand-held devices. For this purpose a test unit 12 inserted as a disposable article can be driven by means of a lancing drive 14 in an in and out reciprocating lancing movement to carry out a skin puncture during which the blood sample collection is monitored by means of a control unit 16 and the measured values are evaluated and displayed on the spot for the user. The success rate after a faulty collection process can be considerably improved by carrying out a second puncture a short time after the first reciprocating puncture.

Figure 1:
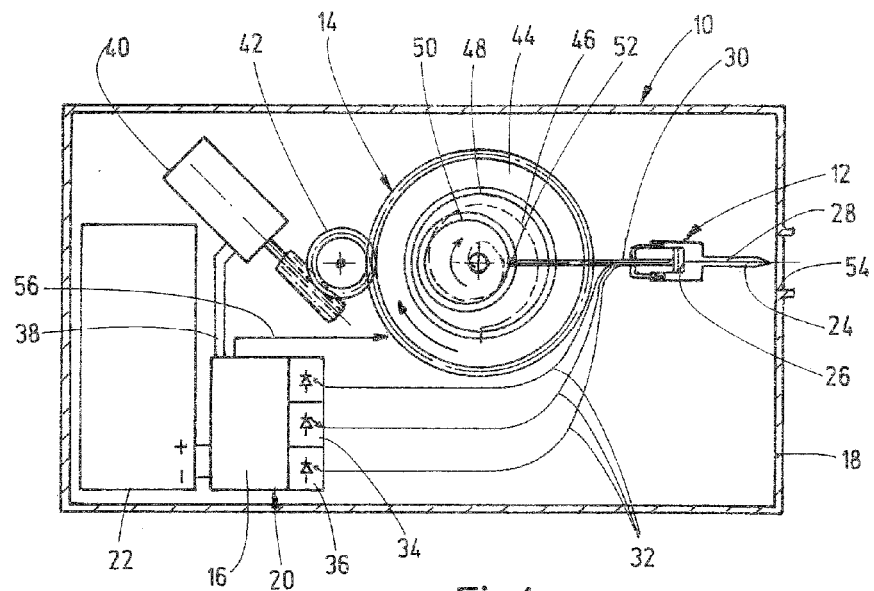
FIG. 1 shows a medical test system with a device for puncture repetition for blood sugar tests in a diagrammatic representation.

FIG. 1 illustrates as a block diagram the hand-held device comprising a housing 18, lancing drive 14, measuring device 20 and energy supply 22. In addition, the disposable test units 12, that are preferably exchangeable in a magazine, form a component of the analytical test system 10.

Each test unit 12 comprises a lancing element 24 and a sensor element 26 arranged thereon which is used up after an analysis. The lancing element 24 configured as a flat shaped part has a groove-shaped capillary channel 28 in its tip area that is open on one side as a collecting structure for body fluid. The capillary channel 28 has a holding volume of less than 100 nl and ends proximally on a dry-chemical detection field of the sensor element 26 which can be coupled from the rear side to the reflection photometric measuring device 20. The U-shaped base of the lancing element 12 can be docked onto a push rod 30 of the lancing drive 14 that can be moved forwards and backwards and at the same time an optical connection to the measuring device 20 is made by means of the light guide 32.

The measuring device has an LED 34 as a light source and two photodiodes 36 as the light receivers for the reflectometric detection of measurement signals. The photodiodes 36 are aligned via light guides 32 onto different detection areas or spots on the detection field of the sensor element 26. The received measurement signals can be qualitatively evaluated with regard to the presence of a blood sample on the detection field as well as quantitatively evaluated with regard to the glucose content in the microprocessor-supported measuring device 20 as will be further elucidated in more detail below. An adjustment unit 38 is provided on the output side to actuate the lancing drive 14.

The lancing drive 14 comprises a direct current motor 40, a gear mechanism 42, a tensioning rotor 44, a spiral spring 46, a guiding cam 48 with an eccentric guiding cam in the form of a circular slot 50 into which a rear control pin 52 of the push rod 30 engages.

The tensioning rotor 44 tensions the spiral spring 46 as an energy store while the guiding cam rotor 48 is held rotationally fixed. In order to trigger a skin puncture, the guiding cam rotor 48 is released for a rotation such that the push rod 30 transfers a reciprocating lancing movement onto the lancing element 24. In this process the tip of the lancing element penetrates into the skin of a body part, e.g., a finger tip pressed against the housing opening 54 and collects the capillary blood or optionally tissue fluid released into the puncture wound in the distal section of the collecting channel 28. If necessary a second puncture can be triggered within a short time by actuating suitable adjusting elements 56 for example in the form of control stops and control cams which are known from EP 1669028 where the guiding cam rotor 48 executes a new rotation for a second reciprocating lancing movement using the residual tension of the spiral spring 46. The lancing element 24 is optionally completely retracted from the body tissue between the first and second puncture.

Figure 2:
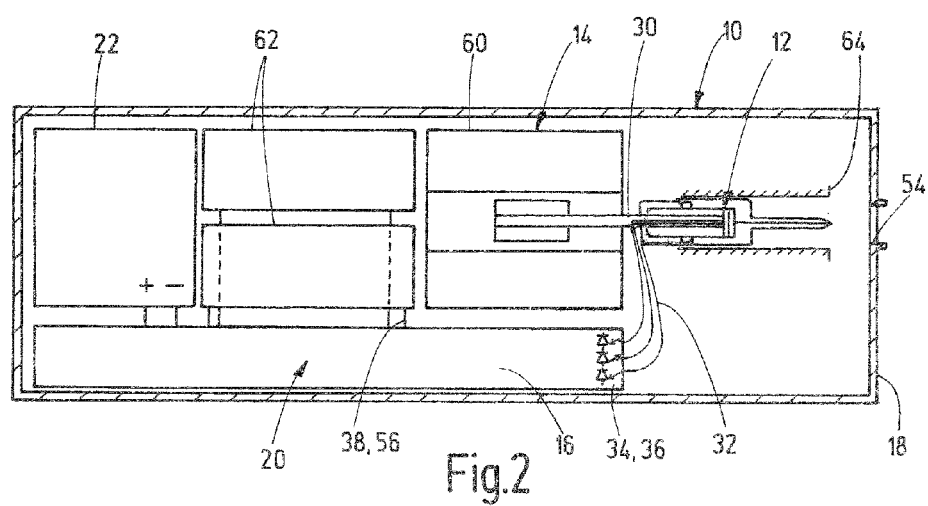
FIG. 2 shows a further embodiment of the test device.

In the embodiment according to FIG. 2 the same or similar parts are given the previously used reference numerals. This example differs essentially only in that instead of a mechanical drive train for the lancing movement, a linear motor 60 is used as a direct drive for the lancing unit 12 coupled via the push rod 30, and that two energy stores 62 in the form of capacitors provide the necessary drive energy in parallel for in each case one reciprocating lancing movement without the battery 22 having to be particularly powerful. A guide 64 which is not shown in FIG. 1 for the sake of clarity is provided to limit the movement to a linear lancing movement.

It is also conceivable that the system switches back and forth alternately between the two energy stores 62. The advantage would be that in the normal case (second puncture unnecessary) always one of the two stores would already be filled up. This allows the system to fill the residual store with less effort when switched on or off. Electrical or electromagnetic energy stores are particularly advantageous for this because they can be activated and switched on by a simple electric circuit.

The examples of FIGS. 1 and 2 allow a puncture repetition in a time interval of less than 1 second when the control device 16 detects insufficient sample collection. In a further concept that is not shown separately a brushless direct current motor is used such as those that are used to drive CD drives or hard disk drives. Such a motor has a small, flat structural design and is therefore well-suited for accommodation on a circuit board. Its other advantages are high efficiency and its tolerance towards brief periods of overcurrent. In this case approximately ten-fold the continuous motor power can be applied making it possible to carry out a puncture repetition in the said time interval of less than 1 second.

Figure 3:
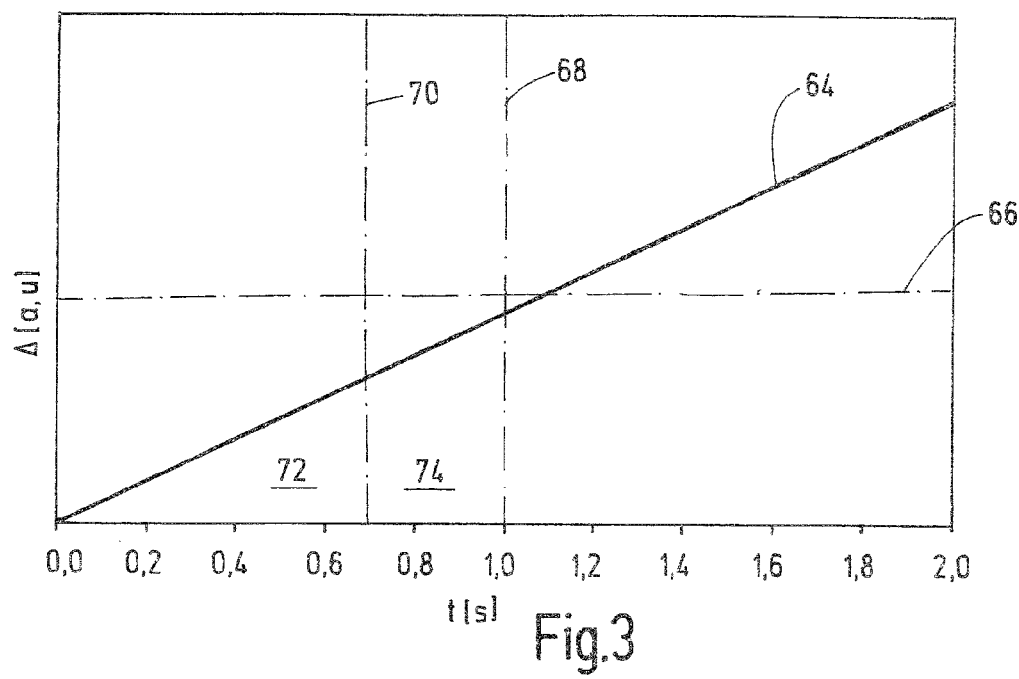
FIG. 3 shows a diagram of the time-dependent measurement deviation in conjunction with various thresholds for the puncture repetition.

The diagram of FIG. 3 illustrates various surprising relationships in the puncture repetition. Water evaporation from the sample during transport from the wound to the test field results in an increase in the measuring inaccuracy Δ. The longer the transport path 28 and the slower the sample transfer, the more water evaporates from the sample liquid and thus falsifies the measurement result approximately linearly over time (increasing curve 64). In this connection the threshold limit 66 specifies a falsification of the measured value that is still acceptable (imprecision threshold).

If the sample transfer after the first puncture prematurely comes to a standstill, after-dosing is only possible for a limited time because otherwise the blood front in the capillary 28 would dry up and not allow further transport. Findings of the applicant indicate that an interruption of sample transfer of 2 s results in an irreversible standstill of the blood front, whereas the blood front starts flowing again in the case of a shorter interruption of less than 1 s. This time limit (after-dosing threshold) is referred to as 68 in FIG. 3.

Feedback in the error detection should be so rapid that the user notices nothing of a required puncture repetition. This recognition threshold 70 is at about 0.7 s.

Thus, in the ideal case the measuring window 72 is used in which all limits 66, 68 and 70 are adhered to. The larger time window 74 incorporates the utilizable range without taking into account the ability of the user to recognize the puncture repetition.

For this purpose suitable configuration of the channel 28 (in particular its length, capillarity and wettability) should ensure that the duration of the sample transport is less than 0.3 s. The optical evaluation of the detection field of the sensor element 26 by means of reflectance measurement additionally allows a speedy check of the wetting state because the wetted field causes an immediate jump in reflectance which only afterwards undergoes a color change which can be used to determine the blood sugar value.

Figure 4:
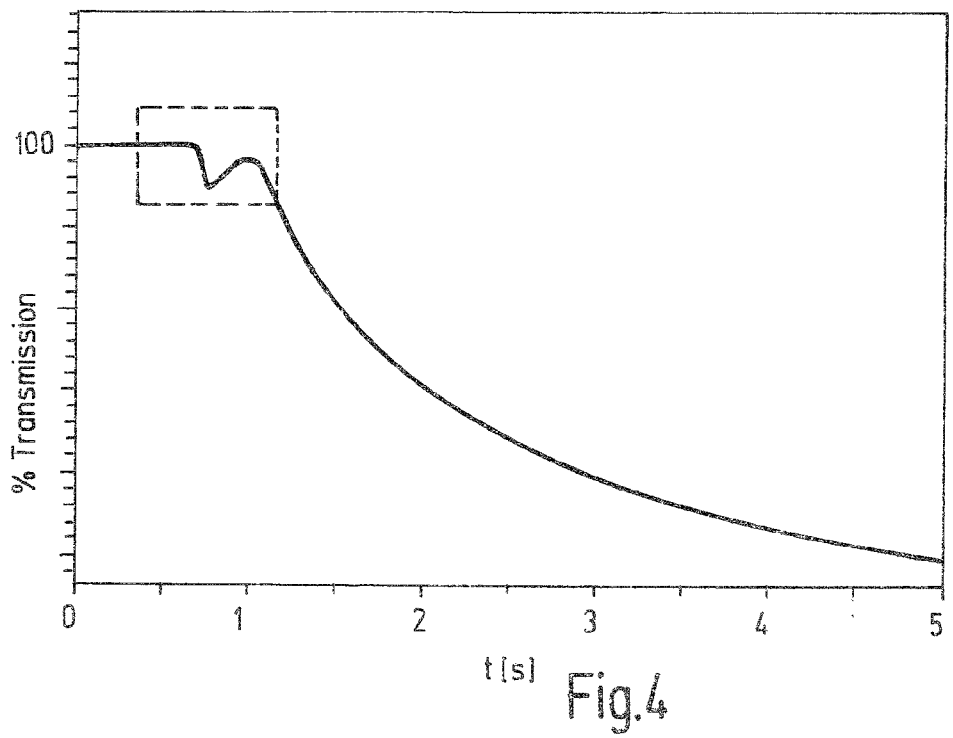
FIG. 4 shows the time course of a measurement signal during the photometric measurement of blood sugar.

The dashed window in FIG. 4 shows the area of a measurement curve that can be used for this case decision. The start value normalized to 100% corresponds to the measured value at the time of the first puncture at t=0 s. In this example the measured value decreases significantly after 0.7 s due to the wetting of the detection field which is referred to here as a step-change or jump in reflectance. After a brief recovery, color development of the test chemistry starts and the curve decreases continuously. Thus a short time after the first puncture it is also possible to decide whether an adequate amount of blood has reached the sensor element or whether a repeat puncture should be carried out.

The case decision for the second puncture is expediently left to an internal system control loop, for example a software routine because it can decide more rapidly with less error than the user himself. Optionally such an automated mechanism can be deactivated by a hardware or software switch that is not shown.

Figure 5:
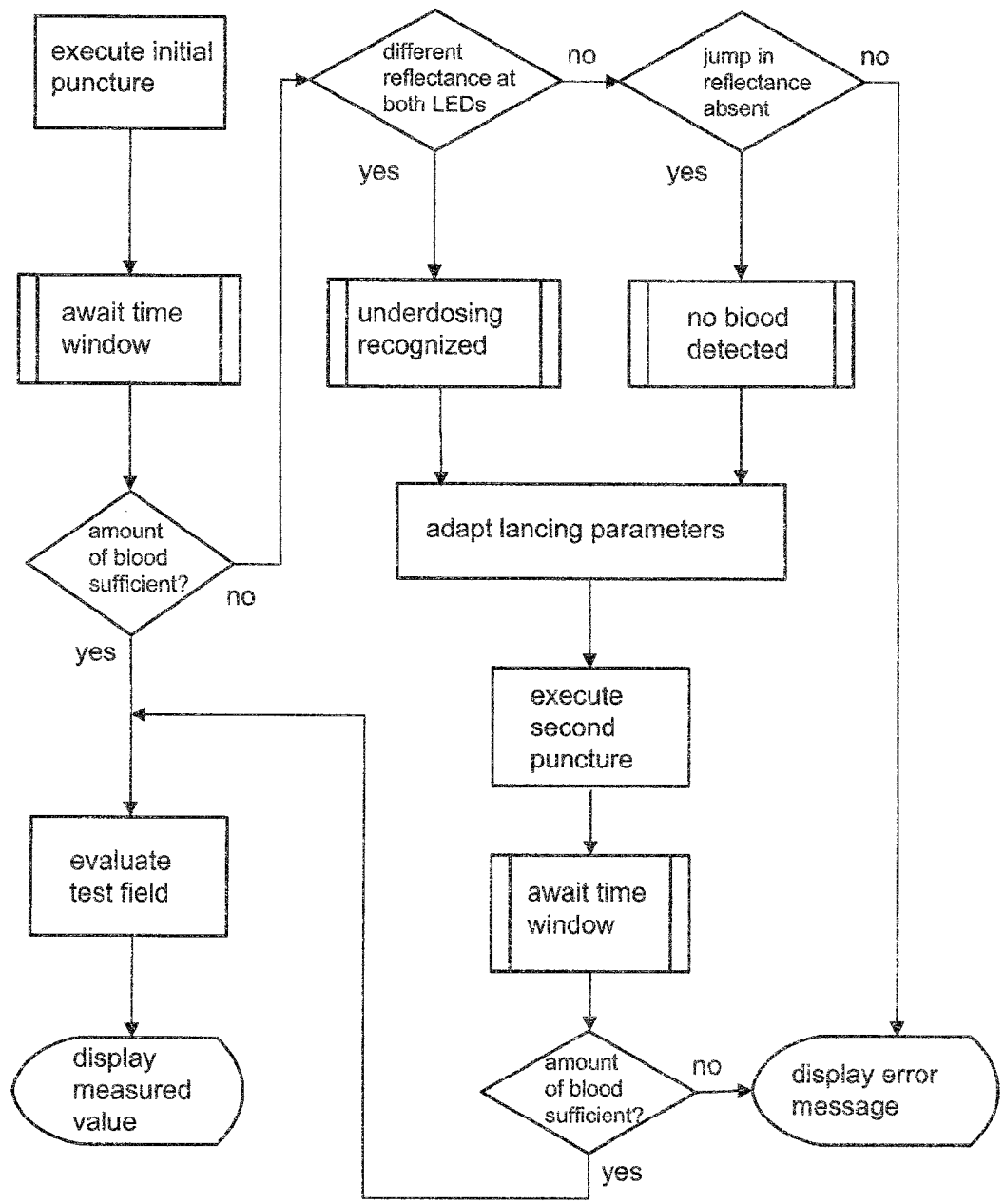
FIG. 5 shows the process for puncture repetition in a flow diagram.

As shown by the flow diagram FIG. 5 as an example, the lancing process can be controlled by the control unit 16 depending on the fault. If no blood at all was collected in the first puncture, then this is detected by the absence of a step-change in reflectance in the predefined time window. In this case it is probable that the lancing depth in the skin was not sufficient and the system can prepare a second puncture with an increased penetration depth. However, it is also conceivable to change the dynamic lancing profile accordingly for example by a longer dwell time of the lancing element 24 in the tissue.

If the amount of blood collected in the first puncture is too small, this results in a step-change in reflectance on the detection field in the predefined time window but the wetted area is very small. This case can be detected using two laterally displaced detection areas in which underdosing results in different reflectances and conversely adequate dosing results in a matching reflectance. If an underdosing has been detected, the system can prepare a second puncture. The lancing parameters can be corrected accordingly but do not have to be subject to the same rules as in the case described above. A repeat puncture with the parameters used for the first puncture may already be sufficient especially in the case of blood underdosing. The query about the amount of blood should be completed in less than 1 s even in the case of a second puncture, such that the user can remove his finger from the lancing opening 54. The further evaluation and subsequent display of the measured value can then take place in a larger time window of several seconds.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medical test system, comprising:
    a lancing element that can be inserted into body tissue to collect body fluid;
    a lancing drive for the lancing element;
    a sensor element for body fluid, the sensor element being arranged on the lancing element and generating a control signal responsive to the presence of body fluid wherein the control signal indicates whether body fluid is present or absent; and
    a control unit coupled to the sensor element, the control unit configured for detecting the control signal, the control unit further programmed to determine whether a sufficient amount of body fluid has been collected or a fault in the collection of body fluid has occurred;
    wherein, when a fault in the collection of body fluid is determined to have occurred by the control unit after a first reciprocating lancing movement, the control unit actuates the lancing drive in an automatic second reciprocating lancing movement, the first and second reciprocating lancing movements having a repetition interval of less than 1 second, and wherein the repetition interval defines a non-zero time period beginning with initiation of the first reciprocating lancing movement and concluding with initiation of the second reciprocating lancing movement;
    when the control unit determines that a sufficient amount of body fluid has been collected after the first reciprocating lancing movement, the body fluid is evaluated by the control unit without conducting a second reciprocating lancing movement; and
    when the control unit actuates the lancing drive in an automatic second reciprocating lancing movement, the control unit makes a second determination whether a sufficient amount of body fluid has been collected or a fault in the collection of body fluid has occurred after the passage of a second non-zero time period following the second reciprocating lancing movement and wherein the control unit evaluates the body fluid if the second determination finds that a sufficient amount of body fluid has been collected after the second reciprocating lancing movement and wherein the control unit generates an error message if the second determination finds that a fault in the collection of body fluid has occurred after the second reciprocating lancing movement.

2. The medical test system of claim 1, wherein the repetition interval is less than 700 ms.

3. The medical test system of claim 1, wherein the repetition interval is less than 500 ms.

4. The medical test system of claim 1, wherein the sensor element is fluidly connected to a section of a collecting channel for body fluid formed on the lancing element.

5. The medical test system of claim 1, wherein the control signal changes discontinuously in reflectance when the sensor element is wetted with body fluid.

6. The medical test system of claim 5, wherein the discontinuous change in reflectance comprises a step-change.

7. The medical test system of claim 1, wherein the sensor element is connected to the control unit by at least one signal conductor during the lancing movement of the lancing element.

8. The medical test system of claim 7, wherein the at least one signal conductor comprises a light guide.

9. The medical test system of claim 1, wherein the sensor element has two or more detection areas arranged spaced apart from one another to detect a two-dimensional load of body fluid.

10. The medical test system of claim 1, wherein the fault comprises the control unit determining an absence of wetting or an inadequate wetting of the sensor element with body fluid.

11. The medical test system of claim 1, further comprising a switch which can be used by a user to deactivate the control unit.

12. The medical test system of claim 1, wherein the control unit has a control loop which automatically adapts lancing parameters for the second lancing movement.

13. The medical test system of claim 1, wherein the lancing drive has an energy store dimensioned for multiple punctures.

14. The medical test system of claim 1, wherein the lancing drive has several energy stores each individually dimensioned for a respective single puncture.

15. The medical test system of claim 1, wherein the lancing drive has a brushless direct current motor that can be temporarily subjected to an overcurrent.

16. The medical test system of claim 1, wherein the sensor element has a detection field for a component of the body fluid, and wherein the component as well as the wetting state of the detection field with body fluid can be detected by a unitary measuring unit.

17. The medical test system of claim 1, wherein the lancing element has a collecting volume of less than 100 nl.

18. The medical test system of claim 1, wherein the lancing element has a capillary collecting channel to transfer the body fluid onto the sensor element in a transfer time of less than 0.3 s after skin puncture.

19. A method of using a test system of the type having a lancing element that can be inserted into body tissue to collect body fluid and a lancing drive for driving the lancing element in a reciprocating puncture movement, the method comprising:

driving the lancet in an initial reciprocating puncture movement with the lancing drive to puncture the body tissue;

collecting body fluid with the lancet after the initial reciprocating puncture movement;

using a sensor of the lancet to detect body fluid that has been collected with the lancet after the initial reciprocating puncture movement;

using a control unit that is connected to the sensor to determine whether a sufficient amount of body fluid has been collected or a fault in collecting body fluid has occurred after the initial reciprocating puncture movement;

wherein, when a fault is determined to have occurred after the initial reciprocating puncture movement by the control unit, driving the lancet in a second reciprocating puncture movement, the initial and second reciprocating puncture movements having a repetition interval of less than 1 second, and wherein the repetition interval defines a non-zero time period beginning with initiation of the initial reciprocating puncture movement and concluding with initiation of the second reciprocating puncture movement;

when the control unit determines that a sufficient amount of body fluid has been collected after the initial reciprocating puncture movement, the body fluid is evaluated by the control unit without conducting a second reciprocating puncture movement; and when the lancet is driven in a second reciprocating puncture movement, the control unit determines whether a sufficient amount of body fluid has been collected or a fault in collecting the body fluid has occurred after the second reciprocating puncture movement and, when the control unit determines that a sufficient amount of body fluid has been collected after the second reciprocating puncture movement, the body fluid is evaluated by the control unit and, when the control unit determines that a fault has occurred after the second reciprocating puncture movement, the control unit generates an error message.

20. The method of claim 19, wherein the repetition interval is less than 700 ms.

21. The method of claim 19, wherein the repetition interval is less than 500 ms.

22. The method of claim 19, further comprising generating a control signal that changes discontinuously in reflectance when a detection field of the sensor is wetted with body fluid.

23. The method of claim 19, further comprising arranging two or more detection fields spaced apart from one another to detect a two-dimensional load of body fluid.

24. The method of claim 19, further comprising, before the second reciprocating puncture movement, automatically adapting lancing parameters for the second reciprocating puncture movement.

25. The method of claim 19, wherein the step of determining a fault comprises determining inadequate wetting of a detection field of the sensor.

26. The medical test system of claim 1, wherein the first reciprocating lancing movement is adapted to puncture the body tissue.

27. The method of claim 19, wherein, when the sensor detects an insufficient collection of body fluid, the control unit determines that a fault has occurred.

* * * * *